United States Patent [19]

Geary et al.

[11] Patent Number: 4,722,836

[45] Date of Patent: Feb. 2, 1988

[54] SUSPENSION TYPE ANTIPERSPIRANT STICK

[75] Inventors: Daniel C. Geary, Randolph, N.J.; Helga Krevald, Tarrytown, N.Y.; Peter P. Walters, Jr., Neshanic Station, N.J.

[73] Assignee: American Cyanamid Company, Stamford, Conn.

[21] Appl. No.: 424,696

[22] Filed: Sep. 27, 1982

Related U.S. Application Data

[63] Continuation of Ser. No. 121,850, Feb. 15, 1980, abandoned, which is a continuation-in-part of Ser. No. 858,581, Dec. 8, 1977, abandoned.

[51] Int. Cl.[4] .......................... A61K 7/32; A61K 7/34; A61K 7/36; A61K 7/38
[52] U.S. Cl. .............................. 424/68; 424/DIG. 5; 424/65; 424/66; 424/67
[58] Field of Search ............................ 424/68, DIG. 5

[56] References Cited

U.S. PATENT DOCUMENTS

| | | | |
|---|---|---|---|
| 3,641,239 | 2/1972 | Mohrlok | 424/184 |
| 4,126,679 | 11/1978 | Davy et al. | 424/66 |
| 4,151,272 | 4/1979 | Geary et al. | 424/66 |

OTHER PUBLICATIONS

Janistyn, Riechstoffe Seifen Kosmetika, 1951, Bd. 2, pp. 232 to 234, 409 & 410.

*Primary Examiner*—Dale R. Ore
*Attorney, Agent, or Firm*—C. J. Fickey

[57] ABSTRACT

Wax-like antiperspirant composition sticks having uniformly distributed astringent salt suspension throughout the stick composition.

16 Claims, No Drawings

SUSPENSION TYPE ANTIPERSPIRANT STICK

This is a continuation of application Ser. No. 121,850, filed Feb. 15, 1980, which is a continuation-in-part of application Ser. No. 858,581, filed Dec. 8, 1977, both now abandoned.

This invention relates to improvements in the manufacture of solid antiperspirant and deodorant stick compositions. The invention further relates to wax-like compositions useful for antiperspirant sticks which have suspended therein an inorganic astringent salt having a more even distribution of said salt in the product to improve the efficacy of such compositions.

In general antiperspirant preparations in the form of sticks consist of wax-like components, usually hydrophobic in nature, which function mainly as a base for an active ingredient. In the case of antiperspirants the active ingredient is normally an astringent, such as aluminum chlorhydroxide or another similarly used compound. The wax-base may, of course, consist of many ingredients to provide specific properties in addition to its primary function British Patent No. 1,156,812 described a cosmetic or pharmaceutical stick in which the base consists of mixtures of polyglycol esters of fatty acids, for example $C_{12}$ to $C_{22}$ fatty acids, such as stearic acid, and polyglycol esters of wax acids, such as Montanic wax. The patentees additionally disclose that fatty alcohols, such as stearyl alcohol, may be incorporated as well as certain ingredients that care for the skin or improve the absorbability of the active ingredient.

The polyglycol esters of fatty acids and wax acids are obtained by esterification thereof with alkylene oxides or polyethylene glycols, built up from 2 to 100, preferably 3 to 30 molecules of ethylene oxide. Thus, the esters have the structure:

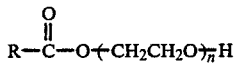

wherein R represents the aliphatic portion of the alcohol and n is an integer from 2 to 100.

Briefly, such antiperspirant sticks are generally produced by forming a molten mass of a mixture of the ingredients constituting the base and having the finely divided astringent salts suspended throughout the mass. Such salts are normally of the order of about 44 microns in particle size or 0.5 meters/gram surface of the BET method or 1.6 meters/gram by the mercury penetration porosimetry method. This molten mixture is then poured into molds and allowed to cool and harden to shape and form the final stick product. The actual manufacturing process includes numerous steps, including maintaining a large quantity of the composition in a molten state in one or more holding tanks while the pouring operation is taking place, and maintaining the poured composition in the molds until the temperature of the molten material becomes low enough to form a solid product, possibly by auxilliary cooling.

The ideal stick product should have an even distribution of astringent salt solids distributed throughout. However, it has been found that the percentage distribution of salt solids varies from the upper to lower portion in commerically available antiperspirant sticks. The variation in salt solids content each end of the stick may vary by as much as 50 percent. This results in differing dosage application of active salts to the skin and therefore in differing degrees of efficacy and is not desirable.

Moreover, settling of the salt solids may also take place in the heated holding kettles, causing flow problems or further complicating the problem of obtaining an even distribution of active astringent salt solids in the manufactured product.

It has been found that homogeneous sticks can be produced when the particle size distribution of the solid astringent has a surface area that equals or exceeds 2.0 square meters/gram as measured by the BET nitrogen adsorption method or 3.0 square meters/gram when measured by the mercury penetration porosimetry technique.

These surface area measurements apply regardless of the density of astringent salts. The large surface area salts produce an even distribution of the salts without the use of special suspending agents such as fumed silica and/or clays. Moreover, the greatly increased surface area of the active salts results in a more efficient concentration/unit area at the same weight level than larger particle salts and thus in greater improve efficacy. A more even distribution also results in a more cosmetically appealing stick product.

The principal of the present invention is applicable with any antiperspirant stick of fatty aclohol or ester composition formed in a molten state and having active astringent salts suspended therein.

Among the useful astringents are aluminum sulfate, aluminum chloride, aluminum chlorhydrate, aluminum sulfocarbolate, aluminum-zirconium chlorhydrate, zinc chloride, zinc sulfocarbolate, zinc sulfate, zirconium salts, such as zirconium chlorhydrate, combinations of aluminum chloride and aluminum-zirconium chlorhydrate, aluminum-zirconium chlorhydrogylcinex and the like. In the aluminum chlorhydrate, and aluminum-zirconium chlorhydrate, the ratio of aluminum to chloride may range from 2.1:1 to 0.9:1 and ratio of aluminum to zirconium may range from 2.5:1 to 10.5:1. Aluminum chlorhydrate is preferred.

The active ingredient may be used in amounts up to about 35% by weight, although normally from about 15 to 25% by weight is used. In any case, sufficient should be added to provide a 20% reduction in perspiration in 50% of the population. The sticks of the present invention containing about 25% aluminum chlorhydrate are also excellent deodorants.

As previously indicated, the antiperspirant base may be of various types, for example as described in copending commonly assigned application Ser. No. 710,951, filed Aug. 2, 1976, which comprises fatty alcohol base, such as stearyl alcohol or cetyl alcohol or mixture thereof; a polyethoxylated fatty alcohol, such as polyethoxylated stearyl or cetyl alcohol, or mixture thereof, containing from about 100 to 200 moles of ethylene oxide per mole of said fatty alcohol; an astringent material and a volatile silicone. The polyethoxylated alcohol has the formula

wherein R represents an alkyl radical of 12 to 22 carbon atoms. The corresponding fatty acids, esters, fatty di-, tri-, and polyols and fatty materials with both hydroxyl and carboxyl groups may also be used in place of the polyethoxylated alcohol. Alternatively, the fatty alcohol may be replaced in part, depending on the hardness of the stick desired, with up to about 5 percent by weight of a modified clay, such as a montmorillonite clay, for example the Bentones (National Lead Ind.), which are reaction products of the clay with dimethyl distearyl ammonium chloride; or, all of the fatty alcohol may be replaced with the ethoxylated fatty alcohol and the hardness adjusted with the Bentones. In any case, no more than about 5 percent by weight of the Bentones should be used. It should be emphasized, however, that as the ethylene oxide content of the ethoxylated fatty alcohol increases the hardness of the product will increase also.

The following specific examples illustrate the invention:

EXAMPLES 1 TO 3

Stearyl alcohol, ethoxylated stearyl alcohol and the cyclic silicone pentamer were melted together at 65° C. and kept agitated. The aluminum chlohydroxide was added at 65° C. and stirred until homogeneously dispersed. Finally, the fragrance was added and the batch passed through an in-line shear flow pump at 65° C. (at least one pass is required). The batch was then allowed to cool to 52°-55° C., poured into suitable containers and then cooled to room temperature.

The stick ingredients and amounts are shown in Table I with the exception of the aluminum chlorhydroxide(ACH). The amount of ACH maintained at approximately 26% and the surface area in meters/gram of the ACH was varied to determine its effect on ACH distribution throughout the solid antiperspirant stick. The surface area was measured both by the BET nitrogen adsorbtion method and the mercury penetration porosimetry method. The results are shown in Table II.

TABLE I

| | percent | | |
|---|---|---|---|
| | I | II | III |
| Stearyl Alcohol (95%) | 20.0 | 20.0 | 20 |
| Steareth-100[1] | 1.0 | 1.0 | 1.0 |
| Volatile Silicone 7158[2] | 53.4 | 53.4 | 53.4 |
| Perfume | 0.6 | 0.60 | .6 |

Aluminum Chlorhydroxide (See Table II)
[1]$CH_3(CH_2)_{17}O-(CH_2CH_2O)_{100}H$
[2]2,4,6,8,10-decamethylcyclopentasiloxane

TABLE II

| | Analysis of A/P Sticks for ACH Distribution | | | | | |
|---|---|---|---|---|---|---|
| | BET | | % ACH | | | |
| Batch # | ($M^2$/g) | MP($M^2$/g) | Top | Middle | Bottom | Average |
| 1085-55-3 | 0.8 | 1.8 | 32.2 | 28.1 | 21.3 | 27.2 |
| 1085-55-2 | 1.0 | 2.1 | 30.8 | 26.4 | 20.6 | 25.9 |
| 1085-55-1 | 1.2 | 2.3 | 30.8 | 27.4 | 21.3 | 26.6 |
| 1085-54-4 | 1.5 | 2.6 | 28.5 | 26.9 | 22.4 | 25.9 |
| 1085-54-3 | 1.75 | 2.8 | 27.8 | 27.2 | 23.0 | 26.0 |
| 1085-54-2 | 2.0 | 3.0 | 26.0 | 26.5 | 25.8 | 26.1 |
| 1085-54-1 | 2.2 | 3.4 | 27.3 | 26.3 | 24.5 | 26.0 |
| 1085-53-5 | 2.3 | 3.4 | 26.2 | 25.7 | 25.8 | 25.9 |
| 1085-53-4 | 2.6 | 3.8 | 26.8 | 26.1 | 25.4 | 26.1 |
| 1085-53-3 | 2.9 | 4.0 | 26.7 | 26.3 | 26.3 | 26.4 |
| 1085-53-2 | 3.1 | 4.3 | 26.5 | 26.4 | 25.9 | 26.3 |
| 1085-53-1 | 3.3 | 4.5 | 26.8 | 25.9 | 25.8 | 26.2 |

The ethoxylated stearyl alcohol in the above formulation may be replaced by stearyl alcohol ethoxylated with 150 or 200 moles of ethylene oxide, or with a similarly ethoxylated cetyl alcohol, with similar results.

We claim:

1. An antiperspirant stick comprising a wax-like base material and an astringent salt, substantially all of said astringent salt having a surface area of at least 2 meters per gram measured by the nitrogen adsorption method or 3 meters per gram measured by the mercury penetration porosimetry method, said astringent salt being uniformly distributed throughout said base material.

2. An antiperspirant stick according to claim 1 wherein said astringent salt is an aluminum salt.

3. An antiperspirant stick according to claim 2 wherein said aluminum salt is aluminum chlorhydroxide.

4. An antiperspirant stick as in claim 1 comprising a wax-like fatty alcohol, said astringent material, a volatile silicone and a polyethoxylated fatty hydrocarbon, ethoxylated with from about 100 to 200 moles of ethylene oxide.

5. An antiperspirant in claim 1 comprising a wax-like fatty alcohol, said astringent material, a volatile silicone, and a polyethoxylated fatty alcohol represented by the formula:

$$R-O-(CH_2CH_2O)_{\overline{n}}H$$

wherein R represents an alkyl radical of about 12 to 22 carbon atoms and n is an integer of about 100 to 200.

6. A cosmetic formulation according to claim 4 wherein said astringent material is aluminum chlorhydroxide.

7. A cosmetic formulation according to claim 4 wherein said volatile silicone is selected from 2,4,6,8-octamethylcyclotetrasiloxane, 2,4,6,8,10-decamethylcyclopentasiloxane, and 2,4,6,8,10,12-dodecamethylcyclohexasiloxane.

8. A cosmetic formulation according to claim 5 wherein R is selected from stearyl and cetyl, or mixtures thereof, and n is 100.

9. A cosmetic formulation according to claim 5 wherein R is selected from stearyl and cetyl, or mixtures thereof, and n is 150.

10. A cosmetic formulation according to claim 5 wherein R is selected from stearyl and cetyl, or mixtures thereof, and n is 200.

11. A cosmetic formulation according to claim 4 wherein said wax-like fatty alcohol is stearyl alcohol.

12. A cosmetic formulation according to claim 4 wherein said wax-like fatty alcohol is cetyl alcohol.

13. A cosmetic formulation according to claim 5 wherein said polyethoxylated fatty alcohol comprises at least about 0.1% by weight.

14. A cosmetic formulation according to claim 12 wherein said polyethoxylated fatty alcohol comprises from about 0.1 to 5% by weight.

15. A cosmetic formulation comprising stearyl or cetyl alcohol, or mixtures thereof, aluminum chlorhydroxide having a, surface area of at least 2 meters per gram measured by the nitrogen adsorption method or 3 meters per gram measured by the mercury porosimetry method, a volatile silicone, and a polyethoxylated fatty alcohol represented by the formula:

$$R-O-(CH_2CH_2O)_{\overline{n}}H$$

wherein R represents an alkyl radical of about 16 to 18 carbon atoms and n is an integer from about 100 to 200, said aluminum chlorhydroxide being uniformly distributed throughout said formulation.

16. A method for forming an antiperspirant stick having a wax-like base and an astringent salt uniformly distributed throughout said base, which comprises adding an astringent salt having a surface area of at least 2 meters per gram measured by the nitrogen absorbtion method or 3 meters per gram measured by the mercury penetration porosimetry method.

* * * * *